United States Patent [19]

Pugia

[11] Patent Number: 5,318,894

[45] Date of Patent: Jun. 7, 1994

[54] COMPOSITION, DEVICE AND METHOD OF ASSAYING FOR PEROXIDATIVELY ACTIVE SUBSTANCES

[75] Inventor: Michael J. Pugia, Granger, Ind.

[73] Assignee: Miles Inc., Elkhart, Ind.

[21] Appl. No.: 472,295

[22] Filed: Jan. 30, 1990

[51] Int. Cl.$^5$ .................. C12Q 1/28; G01N 33/72
[52] U.S. Cl. ........................... 435/28; 436/66; 436/904
[58] Field of Search ............... 435/28; 436/66, 904

[56] References Cited

U.S. PATENT DOCUMENTS

| | | | |
|---|---|---|---|
| 4,288,541 | 9/1981 | Magers et al. | 436/66 |
| 4,310,626 | 1/1982 | Burkhardt et al. | 436/66 |
| 4,615,982 | 10/1986 | Lawrence | 436/66 |

FOREIGN PATENT DOCUMENTS

| | | | |
|---|---|---|---|
| 0123115 | 10/1984 | European Pat. Off. | 435/88 |
| 220143 | 3/1985 | German Democratic Rep. | 436/66 |
| 60-66994 | 4/1985 | Japan | 435/28 |

Primary Examiner—Douglas W. Robinson
Assistant Examiner—Jon P. Weber
Attorney, Agent, or Firm—Roger N. Coe

[57] ABSTRACT

A new and improved test device and method of determining the presence or concentration of a peroxidatively active substance, such as hemoglobin, in a test sample are disclosed. The test device includes a test pad comprising a suitable carrier matrix incorporating an indicator reagent composition capable of interacting with a peroxidatively active substance to produce a detectable or measurable response. In addition, a new and improved indicator reagent composition, comprising an indicator dye, such as a redox indicator, like a benzidine indicator; a hydroperoxide; a metal ion complex; and a phosphorous compound having the general structural formula

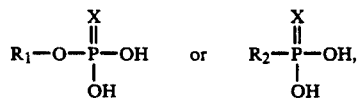

wherein $R_1$ or $R_2$ is selected from the group consisting of hydrogen, an unsubstituted or a substituted alkyl moiety including from one to about twelve carbon atoms, an unsubstituted or a substituted aromatic moiety and a residue of an aliphatic or an aromatic polyhydric compound; and wherein X is O, S or NH; such as glyceryl-2-phosphate or phenyl dihydrogen phosphate, is incorporated into a carrier matrix, or used in a wet phase assay, to provide a more accurate and trustworthy assay of a test sample for a peroxidatively active substance. The improved method and composition are especially useful in the assay of urine for occult blood.

3 Claims, No Drawings

COMPOSITION, DEVICE AND METHOD OF ASSAYING FOR PEROXIDATIVELY ACTIVE SUBSTANCES

FIELD OF THE INVENTION

The present invention relates to a composition, device and method of determining the presence or concentration of a peroxidatively active substance in a test sample. More particularly, the present invention relates to a new and improved method of assaying a liquid test sample, such as urine, for a peroxidatively active substance, like occult blood, by utilizing an oxidation resistant indicator reagent composition. The indicator reagent composition, in a wet phase assay or a dry phase assay, undergoes a detectable or measurable response upon contact with a test sample containing a peroxidatively active substance. The indicator reagent composition of the present invention provides a more accurate and sensitive assay for a peroxidatively active substance by effectively resisting oxidation of an indicator dye present in the indicator reagent composition prior to contact between the indicator reagent composition and the test sample. Accordingly, the improved sensitivity achieved by the indicator reagent composition of the present invention provides an improved method of assaying a test sample for a low concentration of a peroxidatively active substance, such as assaying urine for occult blood.

BACKGROUND OF THE INVENTION AND PRIOR ART

Peroxidase is an enzyme that catalyzes the oxidation of various compounds, such as phenols and amines, by peroxides. In addition, particular compounds have been termed pseudoperoxidases because these compounds behave in a manner similar to the peroxidase enzyme. Accordingly, pseudoperoxides liberate oxygen from hydroperoxides and transfer the oxygen to certain acceptor compounds. Therefore, in general, the pseudoperoxidases are enzyme-like in that they catalyze, or otherwise participate in, reactions between peroxides and oxidizable compounds. The pseudoperoxidases also are termed peroxidatively active substances, and include hemoglobin and its derivatives.

For example, in the assay of urine for glucose, glucose oxidase, in the presence of oxygen, first converts the glucose in the urine to gluconic acid and hydrogen peroxide. Then, the peroxidase enzyme, also present in the assay, catalyzes the interaction between the hydrogen peroxide and an oxidizable dye compound, like o-tolidine. The dye compound, usually essentially colorless in its reduced state, undergoes a color transition upon oxidation, such as to a blue color for o-tolidine, by the peroxidase-catalyzed interaction with hydrogen peroxide. The degree and intensity of the color transition are directly proportional to the amount of hydrogen peroxide generated by the glucose conversion. Then, the amount of hydrogen peroxide generated by the glucose conversion is correlated to the original concentration of glucose in the urine sample.

Similarly, a peroxidatively active substance, like hemoglobin and its derivatives, catalyzes the interaction between a hydroperoxide and an oxidizable dye. In such interactions, the peroxidatively active substance imitates the peroxidase enzyme and catalyzes or otherwise participates in an interaction between the oxidizable dye and the hydroperoxide. The oxygen liberated from a hydroperoxide by a peroxidatively active substance is transferred to an oxidizable dye. The resulting interaction provides a detectable response, such as a color transition, wherein the intensity of the response is indicative of the presence or the concentration of the peroxidatively active substance.

Assays for a peroxidatively active substance are based upon the above-described chromogenic interaction, wherein the degree and intensity of the color transition of the indicator dye are correlated to the concentration of the peroxidatively active substance in the test sample. Assays for a peroxidatively active substance are particularly useful in detecting and measuring low concentrations of blood, often termed "occult" blood, in body fluid samples such as urine, feces or gastrointestinal contents. Although occult blood in urine, feces or vomit usually is not visible to the naked eye, the detection of occult blood is important in the diagnosis of hemorrhages in the stomach, intestines and urinary tract. The hemorrhages are caused, for example, by tumors, ulcers or inflammations of the organ in question. Presently, most methods of determining the presence of occult blood in a test sample are based upon the pseudoperoxidase activity of hemoglobin or myoglobin.

Although protein in urine is the most important indicator of a renal dysfunction, the presence of blood in urine also is an indication of damage to the kidney or urinary tract. Normally, detectable amounts of occult blood are not present in urine, even with very sensitive chemical methods. Blood in the urine can appear as intact red blood cells or as free hemoglobin. Usually the presence of free hemoglobin indicates that the blood cells have ruptured either because of a traumatic passage through the kidney and urinary tract to the bladder, or because the blood cells have been exposed to dilute urine in the bladder that caused the cells to hemolyze.

More particularly, the presence of blood in urine or feces is a symptom of a variety of abnormal conditions, including cancer. The presence of blood in urine, as indicated by a positive test for occult blood, often indicates bleeding in the urinary tract. Free hemoglobin is present in the urine because of renal disorders, infectious diseases, neoplasms, or traumas affecting part of the urinary tract. Free hemoglobin in the urine also can indicate a transfusion reaction, hemolytic anemia, or paroxysmal hemoglobinuria, or can appear from various poisonings or following severe burns. In addition, a positive chemical test for hemoglobin, without the presence of red cells, can indicate myoglobinuria as a result of traumatic muscle injury.

Hemoglobinuria is defined as the presence of free hemoglobin in the urine without red blood cells. In contrast, hematuria is defined as the presence of intact red blood cells in urine. Hematuria is indicative of a specific defect in the microscopic functional unit (the nephron) of the kidney or it is indicative of bleeding in the kidney, the ureter, the bladder or the urethra. The free hemoglobin in the plasma is excreted by the kidney into the urine. In some situations, hemolysis of the red blood cells occurs after the cells have entered the urine. Most urine samples containing red blood cells also contain some hemolyzed occult blood. Presently, the differentiation of trace amounts of blood as cells versus free hemoglobin is of little significance.

Myoglobin, the red respiratory pigment of muscle tissue, is another peroxidatively active substance. Myoglobin is very similar to hemoglobin in its composition and chemical reactions. Myoglobin can be liberated from muscle cells by certain types of injury, and in such cases the myoglobin will circulate in the plasma, and then be excreted in the urine. In addition, certain genetic muscle disorders can cause the muscles to lose myoglobin that subsequently appears in the urine. Myoglobin also is found in the urine after a cardiac infarct.

Hematuria, hemoglobinuria or myoglobinuria depends upon the precise nature of the clinical and pathological disorder and upon the severity of the specific disease or injury. In addition, other peroxidatively active substances also are present in leukocytes and bacteria. Overall, the detection of a peroxidatively active substance is especially important in the diagnosis of diseases and infections of the kidneys and urinary tract.

Therefore, accurate and thorough assays of urine and other test samples for peroxidatively active substances must be available for both laboratory and home use. The assays must permit the detection and measurement of the peroxidatively active substance such that a correct diagnosis can be made and correct medical treatment implemented, monitored and maintained. In addition, it would be advantageous if the assay method could be utilized in a dip-and-read format for the easy and economical, qualitative or quantitative determination of a peroxidatively active substance in urine or other test samples.

Furthermore, any method of assaying for a peroxidatively active substance in urine or other test sample must yield accurate, trustworthy and reproducible results by utilizing an indicator reagent composition that undergoes a color transition as a result of an interaction with a peroxidatively active substance, and not as a result of a competing chemical or physical interaction, such as a preferential interaction with a test sample component other than a peroxidatively active substance or a color transition occurring due to the instability of the indicator reagent composition. Moreover, it would be advantageous if the assay method for a peroxidatively active substance is suitable for use both in wet phase assays and in dry phase reagent strips for the rapid, economical and accurate determination of a peroxidatively active substance in urine or other test sample. Additionally, the method and composition utilized in the assay for a peroxidatively datively active substance should not adversely affect or interfere with the other test reagent pads that are present on multideterminant reagent strips.

Therefore, in order to determine if an individual is excreting a peroxidatively active substance, and in order to monitor the course of medical treatment to determine the effectiveness of the treatment, simple, accurate and inexpensive detection assays for a peroxidatively active substance, like occult blood, have been developed. Furthermore, of the several different assay methods developed for the detection or measurement of occult blood in urine, the methods based on dip-and-read dry phase test strips have proven especially useful because dry phase test strip methods are readily automated and provide reproducible and accurate results.

Some test strips used in assays for peroxidatively active substances have a single test area consisting of a small square pad of a suitable carrier matrix impregnated with an indicator reagent composition comprising an indicator dye, such as a benzidine dye; a hydroperoxide; and a buffer. Other test strips are multideterminant reagent strips that include one test area for the assay of a peroxidatively active substance as described above, and further include several additional test areas on the same strip to permit the simultaneous assay of other urinary constituents. For both types of colorimetric test strips, the assay for a peroxidatively active substance in urine is performed simply by dipping the colorimetric test strip into a well mixed, uncentrifuged urine sample, then comparing the resulting color of the test area of the test strip to a standardized color chart provided on the colorimetric test strip bottle. Occult blood tests usually are included on multideterminant reagent strips to screen urine samples during routine physical examinations because it is important to detect a bleeding condition early.

The test strip method is the simplest and most direct assay for the presence of blood in urine. The test area is impregnated with an oxidizable indicator dye, like tetramethylbenzidine, and buffered hydroperoxide. The test area becomes a green to dark blue color when hemoglobin present in the urine sample catalyzes the oxidation reaction of tetramethylbenzidine by the hydroperoxide. The development of green spots on the test area indicates intact, nonhemolyzed erythrocytes. In accordance with the above-described method, an individual can readily determine, visually, the concentration of a peroxidatively active substance in a urine sample. The color of the test strip is compared with a color chart approximately 1 minute after the test strip is dipped into the urine. The color blocks on the color chart indicate negative, nonhemolyzed trace, hemolyzed trace, small (1+), moderate (2+), and large (3+) amounts of blood. The color chart ranges from orange through green to blue. The assay usually is capable of detecting from about 0.015 to about 0.06 mg/dL (milligrams per deciliter) of free hemoglobin or from about 5 to about 20 intact red blood cells per microliter.

In addition, ascorbate ion, when present, seriously interferes in the above-described assay method for a peroxidatively active compound. It has been found that including certain metal ion complexes in the indicator reagent composition essentially eliminates the ascorbate inferference problem. However, in general, the metal ion complexes also demonstrate peroxidase activity, and behave similarly to peroxidase or the pseudoperoxidases to catalyze the color-forming reaction between a hydroperoxide and an oxidizable dye. Accordingly, although the metal ion complexes eliminate ascorbate interference, the metal ion complexes also can produce false positive assays because the metal ion complexes can catalyze oxidation of the oxidizable dye by the hydroperoxide, thereby producing a color change in the device even though a peroxidatively active substance is not present in the test sample. Furthermore, if a peroxidatively active substance is present in the test sample, erroneously high assay results can occur because of additional dye oxidation mediated by the metal ion complex.

As will be discussed more fully hereinafter, investigators have found that particular ferric ion complexes substantially reduced the false positive and the erroneously high assay results attributed to most metal ion complexes used to eliminate ascorbate interference. However, although the ferric ion complexes effectively eliminated ascorbate interferences and demonstrated a substantially reduced peroxidative activity, the problem of premature oxidation of the oxidizable indicator dye was not completely eliminated. For example, dry phase test strips including a ferric ion complex, a hydroperoxide and an oxidizable indicator dye still demonstrated a color transition after extended storage, or yielded false positive assay results for test samples absent a peroxidatively active substance.

Therefore, it would be extremely advantageous to have a simple, accurate and trustworthy method of assaying urine for low levels of a peroxidatively active substance. Present day test strips for peroxidatively active substances have the disadvantage of premature oxidation of the indicator dye thereby providing false positive assays. Surprisingly and unexpectedly, the composition and method of the present invention essentially eliminate the premature oxidation of the indicator dye, and therefore solve the problem of false positive assays, while still permitting the presence of a compound, like a metal ion complex, to eliminate ascorbate interference. By providing a more accurate method of determining the concentration of a peroxidatively active substance in urine, in an easy to use form, such as a dip-and-read test strip, the urine assay can be performed by laboratory personnel to afford immediate and trustworthy test results. In addition, the test strip method can be performed by the patient at home to more precisely monitor the level of peroxidatively active compounds in urine and/or the success of the medical treatment the patient is undergoing.

As will be described more fully hereinafter, the method of the present invention allows the fast, accurate and trustworthy assay for a peroxidatively active substance by utilizing a test strip that includes a test pad comprising a suitable carrier matrix impregnated with an indicator reagent composition of the present invention. The indicator reagent composition comprises an indicator dye, a hydroperoxide, a metal ion complex and a phosphorus compound including at least two free acid functionalities. The indicator reagent composition is sensitive to low concentrations of a peroxidatively active substance, eliminates ascorbic acid interference with the assay and, surprisingly and unexpectedly, essentially eliminates the premature oxidation of the indicator dye by the metal ion complex and the hydroperoxide that leads to false positive assays. Accordingly, the improved stability of the indicator reagent composition enhances the sensitivity of the assay, thereby providing a more accurate and trustworthy assay for a peroxidatively active substance.

Prior to the present invention, no known method of assaying urine or other test samples for peroxidatively active substances included an indicator reagent composition comprising an indicator dye; a hydroperoxide; a metal ion complex to eliminate ascorbate interference; and a phosphorus compound including at least two free acid functionalities that stabilizes the indicator reagent composition and essentially eliminates the premature oxidation of the indicator dye by the metal ion complex and the hydroperoxide. Consequently, the improved stability of the indicator reagent composition increases the sensitivity of the assay such that accurate and trustworthy assays for peroxidatively active compound are achieved. Although a dry phase test strip including an oxidizable indicator dye, such as o-tolidine or 3,3',5,5'-tetramethylbenzidine; a ferric ion complex; and a hydroperoxide has been used previously, dry phase test strips incorporating these three compounds demonstrated a tendency to prematurely undergo a color transition due to oxidation of the indicator dye. Accordingly, the false positive assay decreased the utility and the sensitivity of the test strip to the peroxidatively active substance in the test sample.

The prior art contains numerous references on the wet phase chemistry and the dry phase chemistry utilized in assaying urine for a peroxidatively active substance. For example, investigators developed wet chemistry assay procedures and dry phase test strip devices for peroxidatively active substances that rely on the enzyme-like catalysis of the peroxidative oxidation of indicator dyes. An example of a wet chemistry assay for a peroxidatively active substance is presented in R. M. Henry, et al., *Clinical Chemistry Principles and Techniques,* 2nd ed., Harper and Row, pp. 1124–1125 (1974). This wet phase assay procedure employs glacial acetic acid as a buffer, diphenylamine as an indicator dye and hydrogen peroxide. Although such wet phase assays are analytically useful, they nevertheless possess severe disadvantages, including poor reagent stability and inadequate analyte sensitivity. For instance, the reagent solutions used in the wet phase assays rapidly decline in stability, and consequently in sensitivity. Therefore, fresh reagent solutions must be prepared after a few days of storage. The continuous preparation of fresh reagent solutions is time-consuming and uneconomical because costly reagents are wasted.

The preferred method of assaying for a peroxidatively active substance utilizes a dry phase test strip device. A typical dry phase test strip is commercially available from the Diagnostics Division of Miles, Inc. under the trademark HEMASTIX®. The test strip comprises a test pad, including a porous carrier matrix, such as a paper matrix, impregnated with a buffered mixture of an organic hydroperoxide and an indicator dye, affixed to a plastic strip or handle. The test pad is immersed in a test sample containing hemoglobin, myoglobin, erythrocytes or another peroxidatively active substance, and the test pad develops a blue color. The intensity of the blue color is proportional to the concentration of the peroxidatively active substance in the test sample. By comparing the color developed in the test pad to a standardized color chart, the analyst can determine, quantitatively, the amount of peroxidatively active substance present in the test sample.

In general, dry phase test strips are more advantageous than the wet phase assays because the test strip format is easier to use, requiring neither the continual preparation of reagents nor the attendant apparatus. In addition, reagent stability is greater in the test strip, thereby resulting in improved assay accuracy, sensitivity and economy. Notwithstanding that present day test strips for determining peroxidatively active substances are substantially more stable and more sensitive than wet phase assays, present day test strips need improvement in the areas of stability and sensitivity. Therefore, it would be a significant advance in the art of diagnostic assays if test strips were even more stable during storage and even more sensitive to peroxidatively active substances. It was towards achieving these improvements that the investigations resulting in the composition, device and method of the present invention were directed.

Several attempts at achieving the above-mentioned goals of increased stability and sensitivity are found in the prior art. For example, in *Chemical Abstracts,* Vol. 85, p. 186 (1976), a two-dip method of preparing a dry phase test strip containing o-tolidine and phenylisopropyl hydroperoxide is described. In this method, filter paper strips impregnated with ethyl cellulose were dipped into an ethanolic solution comprising an indicator, o-tolidine hydrochloride; polyvinylpyrrolidone; a surfactant; and sufficient citrate buffer to provide a pH of 3.7. The impregnated filter paper then was dried, and subsequently was dipped into a second solution containing 1,4-diazobicyclo[2.2.2]octane, phenylisopropyl hydroperoxide and polyvinylpyrrolidone dissolved in an ethanol-toluene mixture. The investigators desired to stabilize the hydroperoxide and indicator with the bicyclooctane compound and the polyvinylpyrrolidone.

Another test strip and method are disclosed in U.S. Pat. No. 3,853,471 to Rittersdorf et al. Rittersdorf described the use of phosphoric acid amides or phosphonic acid amides to stabilize test strips used to assay for peroxidatively active substances. The phosphoric or phosphonic acid amides disclosed by Rittersdorf are triamides and diamides, wherein the substituent amido groups are primarily N-morpholine moieties, and wherein no free acid functionalities remain on the phosphoric or phosphonic acid amide.

Adams et al, in U.S. Pat. No. 3,252,762, disclosed physically encapsulating an organic hydroperoxide within a colloidal material, such as gelatin, to stabilize the test strip. Accordingly, when an aqueous test sample contacts the test strip, the gelatin capsules dissolve, thereby freeing the hydroperoxide for a peroxidatively active substance mediated interaction with an indicator dye. However, the encapsulation process of Adams is time-consuming and requires relatively expensive apparatus and excessive manipulative steps. Each of these prior art disclosures was directed at stabilizing the reagents incorporated into the test pad of the test strip such that the potentially incompatible reagent ingredients, i.e., the hydroperoxide and the indicator dye, would not prematurely interact, and thereby provide a false positive test or render the test strip less sensitive to a peroxidatively active substance.

U.S. Pat. No. 3,975,161 disclosed a test strip comprising a bibulous carrier impregnated with a composition containing an organic hydroperoxide, an acid buffer, a chromogen, a wetting agent, a solid film-forming natural or synthetic polymeric substance and an accelerator. The accelerator is isoquinoline or an isoquinoline derivative. The acid salts or adducts of quinoline and quinoline derivatives also have been described in U.S. Pat. No. 3,986,833 as potentiating agents in reagent compositions for the detection of peroxidatively active substances.

Ku, in U.S. Pat. No. 3,411,887, described the elimination of ascorbate interference with reagent compositions that rely on enzymatic oxidizing substances, such as glucose oxidase, by using an ascorbate "trapping system". The "trapping system" utilizes a heavy metal ion that has an oxidation-reduction potential falling between a redox indicator dye and ascorbate. Suitable heavy metal compounds cited as examples include cobalt, iron, mercury and nickel.

In addition to the disclosure of Ku, the prior art also discloses that metal ions, such as Co(III), are actually pseudoperoxidases. For example, The Merck Index, 9th ed., p. 311 (1976) discloses that Co(III) acetate is used commercially to catalytically decompose cumene hydroperoxide. In addition, a series of Co(III) complexes to catalytically decompose peroxides are reported by K. Lohs, Monatsber. Deut. Akad. Wiss. Berlin, 8, pp. 657–659 (1966). Accordingly, one skilled in the art is taught that using such a metal ion complex in a typical indicator reagent composition for the determination of a peroxidatively active substance would cause a deleterious interaction between the hydroperoxide and the indicator either to produce false positive results or to otherwise render the composition unreactive to the peroxidatively active substance of interest, such as occult blood. In fact, efforts to use mercuric complexes, such as mercuric sarcosinate, in occult blood tests failed.

U.S. Pat. No. 4,587,220, to Mayambala-Mwanika et al., disclosed the use of a chelated ferric ion to eliminate ascorbic acid and ascorbate ion interference in an assay for a perioxidatively active substance. Mayambala-Mwanika disclosed that a ferric chelate, like the ferric chelate of N-(2-hydroxyethyl)ethylenediaminetriacetic acid (Fe-HEDTA), eliminated ascorbate interference and did not produce a false positive test for the peroxidatively active compound. In accordance with the method of Mayambala-Mwanika, a test device for a peroxidatively active substance is prepared by first incorporating the ferric chelate and hydroperoxide into the carrier matrix of the test pad. Then, after drying, the indicator dye is incorporated into the carrier matrix. This two-step method of preparing the test device provided an ascorbate resistant test pad that also demonstrated a sufficient stability to resist a false positive assay result during storage.

Ismail et al., in U.S. Pat. No. 4,755,472, disclosed a stable test pad to assay for a peroxidatively active substance that includes a carrier matrix impregnated with 1,4-diisopropylbenzene dihydroperoxide and a benzidine indicator in a molar ratio of hydroperoxide to indicator of from about 0.9 to 3.0. A ferric chelate also can be included to provide ascorbate resistance. The test pad was stable during storage and does not lead to false positive tests on other test pads present on a multideterminant test strip, such as a glucose test pad based on a peroxidase/potassium iodide indicator.

Lam, in U.S. Pat. No. 4,071,318, disclosed a composition for determining a peroxidatively active substance comprising a hydroperoxide, an indicator dye, and a bicyclic borate ester. Lam theorized that the bicyclic borate ester complexed with the hydroperoxide, thereby precluding the hydroperoxide from interacting with the indicator dye during storage. The improved stability of the composition accordingly provided more accurate assays for a peroxidatively active substance by reducing the premature oxidation of the indicator dye.

In contrast to the prior art, and in contrast to the presently available commercial test strips, the composition of the present invention imparts increased stability to the test strip, and therefore increased sensitivity of the test strip, in the detection and measurement of a peroxidatively active substance in a test sample. The method of the present invention utilizes an indicator reagent composition that effectively resists oxidation of the indicator dye until the indicator dye contacts a test sample containing a peroxidatively active substance. Surprisingly and unexpectedly, the method and composition of the present invention essentially eliminate color formation, or other detectable responses, attributable to a premature indicator dye oxidation by the metal ion complex and the hydroperoxides. Hence, in accordance with the method of the present invention, new and unexpected results are achieved in the dry phase test strip assay, and the wet phase assay, of urine and other test samples for a peroxidatively active substance by utilizing an oxidation resistant indicator reagent composition.

SUMMARY OF THE INVENTION

In brief, the present invention is directed to a new and improved composition, test device and method of determining the presence or concentration of a component in a test sample. The device includes a test pad comprising a suitable carrier matrix incorporating an indicator reagent composition capable of interacting with a test sample component to produce a detectable response. For home use, the indicator reagent composition produces a visually detectable response. For laboratory use, the indicator reagent composition produces a response that is detectable visually or by instrument. The carrier matrix of the test pad comprises a bibulous material, such as filter paper; a nonbibulous material, such as a strip, layer or membrane of a polymerized material; or combinations thereof. An indicator reagent composition is homogeneously incorporated into the carrier matrix, and the carrier matrix then holds the indicator reagent composition homogeneously throughout the carrier matrix while maintaining carrier matrix penetrability by the predetermined component of the test sample.

More particularly, the present invention is directed to a method of assaying urine or other test samples for a peroxidatively active substance by utilizing a new and improved indicator reagent composition. It has been demonstrated that an indicator reagent composition comprising: (a) an indicator dye, like a redox indicator, capable of undergoing a color transition in response to a peroxidatively active substance; (b) a hydroperoxide; (c) a metal ion complex, like a ferric ion complex; and (d) a phosphorus compound having the general structural formula

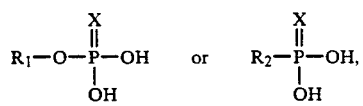

wherein $R_1$ or $R_2$ is selected from the group consisting of hydrogen, an unsubstituted or a substituted alkyl moiety including from one to about twelve carbon atoms, an unsubstituted or a substituted aromatic moiety and a residue of an aliphatic or an aromatic polyhydric compound; and wherein X is O, S or NH; such as glyceryl-2-phosphate or phenyl dihydrogen phosphate; demonstrates improved stability, and therefore increased sensitivity, to a peroxidatively active substance.

In accordance with an important feature of the present invention, a more accurate and reliable qualitative or quantitative determination of a peroxidatively active substance in a test sample is accomplished because the indicator reagent composition effectively resists the color-forming oxidation of the indicator dye prior to contact between the indicator reagent composition and a test sample including a peroxidatively active substance. By utilizing the indicator reagent composition of the present invention in clinical test methods, the qualitative or quantitative assay for a peroxidatively active substance, such as hemoglobin, in urine or other test samples is more accurate because the indicator reagent composition does not yield false positive assays due to premature oxidation of the indicator dye.

Therefore, it is an object of the present invention to provide a new and improved method and test device for determining the relative concentration of a chemical compound in a liquid test sample.

Another object of the present invention is to provide a simple, trustworthy, accurate and reproducible method of assaying urine and other test samples for a peroxidatively active substance.

Another object of the present invention is to provide a method of assaying urine or other liquid test samples for a peroxidatively active substance utilizing a stable, oxidation resistant indicator reagent composition that provides increased sensitivity to the peroxidatively active substance.

Yet another object of the present invention is to provide a method of assaying biological test samples that is sensitive to low concentrations of a peroxidatively active substance and that substantially eliminates false positive assays.

Another object of the present invention is to provide a method of assaying urine or other liquid test samples for occult blood that is sufficiently sensitive to detect occult blood in concentrations as low as about one part of occult blood per one trillion parts of test sample.

Another object of the present invention is to provide a method of assaying urine or other test liquids for a peroxidatively active substance utilizing an indicator reagent composition comprising a metal ion complex, a hydroperoxide, an indicator dye and a phosphorus compound including at least two free acid functionalities wherein the premature oxidation of the indicator dye present in the indicator reagent composition is essentially eliminated.

Another object of the present invention is to provide a method of assaying urine or other test samples by utilizing a stable indicator reagent composition that effectively resists oxidation of the indicator dye prior to contacting the test sample and that, upon contact with the test sample, can interact with a peroxidatively active substance in the test sample and undergo a detectable and measurable color transition to establish the presence or concentration of the peroxidatively active substance in the test sample.

Another object of the present invention is to provide a new and improved test device for interaction with a peroxidatively active substance in a test sample to produce a visible change, such as a change in color, of the test device, indicative of the concentration of the peroxidatively active substance in the test sample.

Another object of the present invention is to provide a composition and test device that are sensitive to low concentrations of a peroxidatively active substance, demonstrate excellent resistance to ascorbate interferences, have excellent storage stability and essentially eliminate false positive assay results for a peroxidatively active substance.

Still another object of the present invention is to provide a stable, oxidation resistant indicator reagent composition capable of undergoing a color transition upon contact with a peroxidatively active substance, wherein the indicator reagent composition comprises an oxidizable indicator dye; a hydroperoxide; a metal ion complex; and a phosphorus compound having the general structural formula

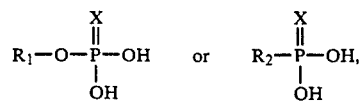

wherein $R_1$ or $R_2$ is selected from the group consisting of hydrogen, an unsubstituted or a substituted aliphatic moiety including from one to about twelve carbon atoms, an unsubstituted or a substituted aromatic moiety and a residue of an aliphatic or an aromatic polyhydric compound, and wherein X is O, S or NH.

The above and other objects and advantages and novel features of the present invention will become apparent from the following detailed description of the preferred embodiments of the present invention illustrating the indicator reagent composition, the test device, and the wet phase and the dry phase assay of liquid test samples for a peroxidatively active substance.

DETAILED DESCRIPTION OF THE INVENTION

In accordance with the method of the present invention, the qualitative or quantitative assay for a peroxidatively active substance, such as hemoglobin and myoglobin, in urine and other test samples is accomplished by utilizing an oxidation-resistant indicator reagent composition comprising an indicator dye, a metal ion complex, a hydroperoxide and a phosphorus compound including at least two free acid functionalities. By employing the indicator reagent composition of the present invention, premature oxidation of the indicator dye by the metal ion complex and the hydroperoxide, prior to contact between the indicator reagent composition and the test sample, is essentially eliminated. The indicator dye, after contacting a test sample including a peroxidatively active substance, readily undergoes a color transition in response to an interaction with the hydroperoxide that is mediated by the peroxidatively active substance in the test sample.

In addition, the metal ion complex included in the indicator reagent composition eliminates ascorbate interference from the assay, and, surprisingly, the metal ion complex does not contribute to the color transition response provided by the peroxidatively active substance in the test sample. Accordingly, the accuracy and the sensitivity of the assay to a low concentration of a peroxidatively active substance are increased. The improved accuracy and increased sensitivity to low levels of a peroxidatively active substance afforded by the method of the present invention are especially useful in urine assays for occult blood.

A commercially useful urine assay for occult blood must be stable, sensitive and resistant to ascorbic acid interferences. The stability and sensitivity requirements for a useful occult blood assay have been defined. For example, a sensitivity of at least 1 part occult blood per trillion parts of urine sample, or, equivalently, for 0.015 mg (milligrams) hemoglobin per deciliter (dL) of urine, or $2 \times 10^{-9}$ moles of hemoglobin per liter (L) of urine, is required. In addition, as previously discussed, ascorbic acid and the ascorbate ion are common interferents with diagnostic tests based on redox indicator dyes. Ascorbic acid interferences in the assay of urine for occult blood are well known in the art and must be eliminated. Ascorbic acid interferes with the oxidation of the indicator dye, and therefore ascorbic acid in a test sample produces an apparent negative result for a peroxidatively active substance. "Ascorbate resistance" therefore is defined as a negligible interference with the color transition of the indicator dye when a urine sample contains as much as approximately 50 mg (milligrams) ascorbic acid per deciliter (dL) of sample.

Ascorbate resistance is imparted to the test device of the present invention by the addition of a metal ion complex to the indicator reagent composition. However, metal ion complexes, like ferric complexes and cobalt (III) complexes, possess inherent peroxidative activity. Therefore the metal ion complex can behave in a similar manner to a peroxidatively active substance, like hemoglobin, and catalyze, or otherwise participate in, the color-forming hydroperoxide oxidation of the indicator dye. Accordingly, the indicator dye can be prematurely oxidized during storage, or a portion of the indicator dye can be oxidized by the metal ion during the assay, to give either a false positive, or an erroneously high assay result. U.S. Pat. No. 4,587,220 to Mayambala-Mwanika et al discloses the use of particular ferric ion complexes, as opposed to complexes of other metal ions, such as cobalt (III), to substantially alleviate the problems of reduced indicator dye stability and of false positive or erroneously high assay results. However, these problems nevertheless still exist in present day methods and devices to assay for peroxidatively active substances. Surprisingly and unexpectedly, it has been found that the composition and method of the present invention essentially eliminates the problem of premature oxidation of the indicator dye by the metal ion complex, such as a ferric ion or a cobalt (III) ion complex, and the hydroperoxide, to provide an accurate and sensitive assay for a peroxidatively active substance in a test sample.

Present day commercial assays for a peroxidatively active substance, like occult blood, can detect hemoglobin concentrations in urine as low as about 0.015 mg/dL. The urine of a healthy individual is free of hemoglobin. Therefore, detecting such a low concentration of hemoglobin in urine is clinically important because hemoglobin in the urine can signify a diseased or damaged condition that should be investigated further. Accordingly, and as will be discussed more fully hereinafter, the method and device of the present invention accurately assay for a low concentration of a peroxidatively active substance in urine. The composition used in the method and device of the present invention is stable, resists ascorbate interference, and undergoes a color transition only in response to the concentration of the peroxidatively active substance in the test sample, thereby providing a sensitive and reliable assay for a peroxidatively active substance.

Furthermore, it will become apparent that in addition to assaying urine, the method and device of the present invention also can be used to determine the presence or quantitive concentration of a peroxidatively active substance in blood plasma or serum, feces, and gastrointestinal contents; and more generally, the peroxidatively active substance concentration of many other biological fluids and semisolids as well. In general, any aqueous test sample, or test sample that is soluble in an aqueous solvent, can be assayed. In accordance with another important feature of the present invention, the method and composition of the present invention can be employed both in aqueous, liquid phase assays and, to achieve the full advantage of the present invention, in dry phase test strip assays to determine the presence or concentration of a peroxidatively active substance in urine or other test samples.

Surprisingly and unexpectedly, it has been found that including a suitable phosphorus compound including at least two free acid functionalities is an indicator reagent composition further comprising a metal ion complex, an indicator dye and a hydroperoxide substantially increases the stability of the indicator reagent composition, and essentially eliminates the present day problem of false positive assays and of erroneously high assay results for a peroxidatively active substance. As will be discussed more fully hereinafter, the phosphorus compounds found to increase the stability of the composition, and to increase the accuracy, sensitivity and reliability of an assay for a peroxidatively active substance, like hemoglobin, are depicted by general structural formulas (I) and (II):

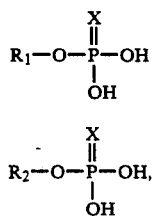

wherein $R_1$ or $R_2$ is selected from the group consisting of hydrogen, an unsubstituted or a substituted aliphatic moiety including from one to about twelve carbon atoms, an unsubstituted or a substituted aromatic moiety, and a residue of an aliphatic or an aromatic polyhydric compound; and wherein X is O, S, or NH.

The method and test device utilizing the composition of the present invention provide a more accurate, trustworthy and clinically significant assay for a peroxidatively active substance because the indicator dye undergoes a color transition only in response to the amount of the peroxidatively active substance present in the test sample, and not to the metal ion complex included in the composition to provide ascorbate resistance. Furthermore, a method of fast, accurate, reproducible and trustworthy assays for a peroxidatively active substance, performable at home or in the laboratory to yield essentially immediate assay results, is achieved.

The method of the present invention utilizes the ability of a peroxidatively active substance to catalyze, or otherwise participate in, a reaction wherein a hydroperoxide releases oxygen, and then transfers the oxygen to oxidize an indicator dye. The oxidation of the indicator dye results in a color transition of the indicator reagent composition, with the degree and intensity of the color transition being directly proportional to the concentration of the peroxidatively active substance in the test sample. Accordingly, the indicator reagent composition of the present invention includes a hydroperoxide and an indicator dye, wherein the indicator dye undergoes a color transition upon conversion to its oxidized form by the mediation of the hydroperoxide and a peroxidatively active substance present in the test sample.

The indicator reagent composition also includes an ingredient to eliminate ascorbate interference with the assay for the peroxidatively active substance. In accordance with the present invention, the ingredient included to eliminate ascorbate interference is a metal ion complex. However, the metal ion complex also possesses a degree of peroxidative activity that can reduce the stability of the indicator reagent composition, or that can produce either false positive or erroneously high assay results. Therefore, in accordance with an important feature of the present invention, the indicator reagent composition also includes a phosphorus compound of general structural formula (I) or (II) that effectively counteracts the peroxidative activity of the metal ion complex in order to provide a stable indicator reagent composition that yields an accurate and reliable assay for a peroxidatively active substance.

The indicator dye included in the indicator reagent composition is limited only in that the indicator dye is capable of undergoing a detectable response, and preferably a chromogenic response, in the presence of a hydroperoxide and a peroxidatively active substance. Accordingly, the indicator dye preferably is a redox indicator that undergoes a color transition upon conversion from its reduced state to its oxidized state by oxygen liberated from the hydroperoxide by the peroxidatively active substance. The indicator dye should be sufficiently stable such that both a hydroperoxide and a peroxidatively active substance are present before a color transition occurs. To achieve the full advantage of the present invention, the indicator dye undergoes a color transition through various detectable and measurable degrees and intensities of color such that the degree or intensity of the color transition can be correlated to the concentration of a peroxidatively active substance in a test sample.

Several indicator dyes are suitable for use in the composition of the present invention, and generally include compounds that are oxidized relatively easily to yield deeply-colored oxidation products. Suitable classes of indicator dyes include, but are not limited to, the benzidine-type indicator compounds and the heterocyclic azine indicator compounds. Examples of the heterocyclic azine indicator compounds include, but are not limited to, bis-(N-ethylquinol-2-one)-azine and (N-methylbenzthiazol-2-one)-(1-ethyl-3-phenyl-5-methyltriazol-2-one)-azine. The benzidine-type indicator compounds include, but are not limited to, for example, benzidine; o-tolidine; 3,3',5,5'-tetra(lower alkyl)benzidine; o-dianisidine; 2,7-diaminofluorene; and mixtures of these and other suitable indicator dyes. The term "lower alkyl", as used above, is defined as an alkyl moiety having from one to about six carbon atoms, including methyl, ethyl, n-propyl, isopropyl and the various butyl, pentyl and hexyl isomers. To achieve the full advantage of the present invention, the redox indicator, 3,3',5,5'-tetramethylbenzidine (TMB), is included in the indicator reagent composition.

The indicator dye usually is present in the indicator reagent composition in a concentration of from about 5 mM (millimolar, or millimoles of indicator dye per liter of indicator reagent composition) to about 60 mM, and preferably in a concentration of from about 20 mM to about 40 mM. It should be understood that the amount of indicator dye in the indicator reagent composition can be less than about 5 mM, or greater than about 60 mM, depending upon the intensity of the color transition that a particular indicator dye undergoes upon oxidation. In general, the amount of indicator dye included in the indicator reagent composition is limited only in that the indicator dye must undergo a detectable color transition for a qualitative assay or, for a quantitative assay, must undergo a measurable color transition in proportion to the amount of peroxidatively active substance in the test sample.

In accordance with another important feature of the present invention, the indicator reagent composition also includes a hydroperoxide. The hydroperoxide is a compound capable of liberating free oxygen. The free oxygen in turn oxidizes the indicator dye to cause a color transition of the indicator reagent composition.

The peroxidatively active substance present in the test sample catalyzes the liberation of free oxygen from the hydroperoxide and transfers the free oxygen to the indicator dye, therefore initiating the color transition of the indicator dye.

Accordingly, a hydroperoxide included in the indicator reagent composition of the present invention should be sufficiently stable such that free oxygen is not liberated in the absence of a peroxidatively active substance. In addition, the hydroperoxide should possess a sufficiently low vapor pressure such that the hydroperoxide does not evaporate, or sublime, from the indicator reagent composition during storage, or after the indicator reagent composition is incorporated into a carrier matrix of a test pad of a dry phase test strip. Furthermore, the hydroperoxide should demonstrate a sufficient sensitivity to detect 1 part of hemoglobin in one trillion parts of test sample in the assay of urine for occult blood.

Therefore, a hydroperoxide useful in the indicator reagent composition of the present invention is selected from among the many well known hydroperoxides. However, the hydroperoxide must be capable of interacting with a peroxidatively active substance in the presence of a suitable indicator dye to produce a detectable response, such as a color transition or a change in the amount of light absorbed or reflected by the test sample. Organic hydroperoxides are preferred. Specific examples of suitable hydroperoxides include, but are not limited to, cumene hydroperoxide, t-butyl hydroperoxide, diisopropylbenzene hydroperoxide, 1-hydroxycyclohexane-1-hydroperoxide, 2,5-dimethylhexane-2,5-dihydroperoxide, paramenthane hydroperoxide, 1,4-diisopropylbenzene monohydroperoxide, p-t-butylisopropylbenzene hydroperoxide, 2-($\alpha$-hydroperoxyisopropyl)-6-isopropylnaphthalene, tetralin hydroperoxide and combinations thereof. In the assay of urine for occult blood, 1,4-diisopropylbenzene dihydroperoxide (DBDH) is the preferred hydroperoxide because of the stability, sensitivity, and nonvolatility of DBDH.

The concentration of a hydroperoxide included in the indicator reagent composition ranges from about 5 mM to about 100 mM, and preferably from about 25 mM to about 75 mM. The specific amount of a particular hydroperoxide included in the indicator reagent composition is dependent upon the physical and chemical properties of the particular hydroperoxide, such as stability, sensitivity towards a peroxidatively active substance and volatility.

Furthermore, in addition to the indicator dye and the hydroperoxide, the indicator reagent composition also includes a metal ion complex to impart ascorbate resistance to the assay. In general, the metal ion complex facilitates oxidation of the ascorbate ion present in the test sample and thereby eliminates the ascorbate interference. Metal ions have inherent peroxidative activity, and, unless complexed, will interact with the hydroperoxide present in the indicator reagent composition to cause the indicator dye to change color. In addition, the prior art teaches that complexed metal ions, other than a complexed ferric ion, interact with a hydroperoxide and an indicator dye to cause a color change.

In accordance with an important feature of the present invention, it is envisioned that essentially any metal ion that can eliminate ascorbate interference, when complexed, can be included in the indicator reagent composition of the present invention to essentially eliminate premature oxidation of the indicator dye. Accordingly, a metal ion useful in the metal ion complex included in the indicator reagent composition is selected from the group consisting of ferric ion, cobalt (III) ion, cupric ion, mercuric ion, stannic iron, nickel (II) ion, lead (II) ion, manganese (III) ion, cadmium (II) ion, zinc (II) ion, molybdenum (V) ion, chromium (IV) ion and vanadium (III) ion, or combinations thereof. In addition, metal ions having a valence state greater than (III) also can be used as the metal ion, as long as the metal ion can be complexed sufficiently to prevent premature oxidation of the indicator dye. To achieve the full advantage of the present invention, the metal ion present in the metal ion complex is the ferric ion.

As stated above, the metal ion must be complexed to prevent premature oxidation of the indicator dye. However, the identity of the complexing agent is not particularly limited and, for example, can include a polycarboxyalkylamine, like ethylenediaminetetraacetic acid or nitrilotriacetic acid; a polycarboxylic acid or salt, like citric acid, oxalic acid, tartaric acid or gluconic acid; a polyhydroxy compound, like sorbitol; a lignosulfonate; a glucoheptonate; bis(dimethylglyoximato); salicylate complexes, like bissalicylaldehydeethylenediiminato; dithioate derivatives; polyethyleneamines, like triethyleneamine; (2-dimethylaminoethyl)aminecobalt (II); a 2,4-pentanedione derivative; a dipyridine derivative; triethylanepyridine amine; a polypeptide containing cysteine, glycine or histidine; a proline derivative; a thiocrown ether, like 1,4,8,11,22,25-octathiacyclooctasane; a triphenylphosphine; or combinations thereof.

In particular, ferric ion complexes useful in the indicator reagent composition include, but are not limited to, the ferric ion polycarboxyalkylamine complexes, such as the ferric ion complexes of N-(2-hydroxyethyl)ethylenediaminetriacetic acid (Fe-HEDTA), ethylenediaminetetraacetic acid (Fe-EDTA), cyclohexylenediaminetetraacetic acid (Fe-CDTA), nitrilotriacetic acid (Fe-NTA), iminodiacetic acid (Fe-IMDA), ethylenediaminediacetic dipropionic acid (Fe-EDDP both $\alpha$ and $\beta$ forms), hydroxyethyliminodiacetic acid (Fe-HIMDA), diethylenetriaminepentaacetic acid (Fe-DTPA), ethylenebis(oxyethylenenitrilo)tetracetic acid (Fe-EGTA), N-(2-acetamido)iminodiacetic acid (Fe-ADA), or combinations thereof. The ferric ion polycarboxyalkylamine complexes are described more fully in U.S. Pat. No. 4,587,220, hereby incorporated by reference. Other suitable ferric ion complexes include ferric citrate, ferric gluconate, ferric glucoheptonate, ferric bissalicylaldehydeethylenediiminato, and ferric triethylenepyridine amine. The preferred ferric ion complexes are Fe-HEDTA and Fe-EDTA. To achieve the full advantage of the present invention, the ferric ion complex Fe-HEDTA is included in the indicator reagent composition of the present invention.

The metal ion complex is included in the indicator reagent composition in an amount ranging from about 0.5 mM to about 50 mM, and preferably in the range of from about 1 mM to about 25 mM. When present in this amount, the metal ion complex essentially eliminates ascorbate interference in the assay of test samples including up to about 50 mg/dL (milligrams per deciliter) ascorbate. In addition, it should be understood that a suitable metal ion complex, like Fe-HEDTA, can be commercially available, and therefore incorporated directly into the indicator reagent composition. Alternatively, the metal ion complex can be produced in situ during manufacture of the indicator reagent composition, such as by independently incorporating a metal ion salt, like ferric chloride hexahydrate (FeCl$_3$.6H$_2$O), and an approximately equimolar amount of a complexing agent, like N-(2-hydroxyethyl)ethylenediaminetriacetic acid (HEDTA), into the indicator reagent composition to form the Fe-HEDTA ferric ion complex. When forming the metal ion complex in situ, the metal ion complex is formed before the uncomplexed metal ion can contact and interact with the hydroperoxide and the indicator dye.

When a composition including only a metal ion complex, a hydroperoxide and an indicator dye is used in a method to assay a test sample for a peroxidatively active substance definite disadvantages become apparent. As previously stated, the metal ion complex is included in the composition to eliminate ascorbate interference through a combined action of the metal ion complex and the hydroperoxide. However, the combination of a metal ion complex and a hydroperoxide also can result in a false positive assay for a peroxidatively active compound due to oxidation of redox indicator dye. For example, aqueous solutions including only a ferric complex, a hydroperoxide and tetramethylbenzidine (TMB) dye produce a blue color due to oxidation of TMB.

Accordingly, indicator dye oxidation by the metal ion complex and the hydroperoxide can introduce severe limitations on the stability of a dry phase test strip and on the process used to manufacture a dry phase test strip. For example, composition ingredients must be incorporated into the carrier matrix in two steps, wherein the first step includes incorporating the metal ion complex and the second step includes incorporating the hydroperoxide and the indicator dye. In addition, if a ferric ion complex is used, the test strip must be buffered to a pH greater than 6.6 to prevent the ferric ion complex from reacting directly with the indicator dye, and thereby producing a large false positive, or blank, reaction. Consequently, until the composition and method of the present invention, no wet phase assays for a peroxidatively active substance employing a redox indicator dye, a metal ion complex and a hydroperoxide were available because of a large background oxidation of the indicator dye. Likewise, dry phase test strips incorporating a redox indicator, a hydroperoxide and a metal ion complex provided false positive, or erroneously high, assay results.

Surprisingly and unexpectedly, it has been found that including a phosphorus compound having at least two free acid functionalities in an indicator reagent composition that further includes an indicator dye, a hydroperoxide and a metal ion complex sufficiently stabilizes the indicator reagent composition such that the indicator reagent composition can be used in a wet phase assay, or in a dry phase test strip assay, of a test sample for a peroxidatively active substance. In general, a phosphorus compound useful in the composition of the present invention is depicted by general structural formulas (I) and (II):

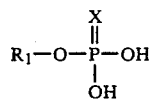

(I)

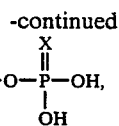

wherein $R_1$ or $R_2$ is selected from the group consisting of hydrogen, an unsubstituted or a substituted aliphatic moiety including from one to about twelve carbon atoms, an unsubstituted or a substituted aromatic moiety and a residue of an aliphatic or an aromatic polyhydric moiety, and wherein X is O, S or NH. A phosphorus compound of general structure (I) or (II) is included in the indicator reagent composition of the present invention in a concentration ranging from about 50 mM to about 500 mM, and preferably from about 100 mM to about 400 mM. To achieve the full advantage of the present invention, a suitable phosphorus compound is present in a concentration ranging from about 150 mM to about 300 mM. When present in a concentration of at least 50 mM, a phosphorus compound of general structural formula (I) or (II) imparts improved stability to the indicator reagent composition. In addition, a suitable phosphorus compound can be included in the indicator reagent composition in a concentration greater than about 500 mM without adversely affecting the indicator reagent composition or the method of the present invention. However, further improvements in the stability of the indicator reagent composition are not demonstrated and the increased concentration of the suitable phosphorus compound therefore is wasted.

As will be demonstrated more fully hereinafter, a phosphorus compound as depicted by general structural formulas (I) and (II) imparts improved stability to an indicator reagent composition used to assay a test sample for a peroxidatively active substance. It also has been found that the corresponding diesters and triesters of the phosphorus compounds depicted in general structural formulas (I) and (II) do not provide the advantages and benefits demonstrated by a monoester or acid phosphorus compound of general structural formula (I) or (II). However, it is envisioned that the thio (X=S) or the imino (X=NH) derivatives of the phosphorus compounds of general structure formula (I) or (II) also are useful in the indicator reagent composition of the present invention. Therefore, in accordance with an important feature of the present invention, a suitable phosphorus compound that provides a stable indicator reagent composition is a phosphorus compound of general structural formula (I) or (II) having at least two free acid functionalities. Accordingly, the phosphorus compound of general structural formula (I) wherein $R_1$ is hydrogen, i.e., phosphoric acid, has three free acid functionalities, and also is useful in the composition of the present invention. Likewise, the phosphorus compound of general structural formula (II) wherein $R_2$ is hydrogen, i.e., phosphonic acid, has two free acid functionalities, and is useful in the composition of the present invention.

It also has been found that the substituent $R_1$ on the phosphorus compound of general structural formula (I) or the substituent $R_2$ on the phosphorus compound of general structural formula (II) can be an aliphatic moiety including from one to about twelve carbon atoms. Furthermore, as the number of carbon atoms included in the aliphatic moiety increases, the more effectively a phosphorus compound of general structural formula (I)

or (II) stabilizes the indicator reagent composition of the present invention. Accordingly, a phosphorus compound of general structural formula (I) or (II) wherein $R_1$ or $R_2$ is an aliphatic moiety including from about 5 to about 10 carbon atoms is preferred. It is theorized that the improved stability imparted by a phosphorus compound of general structural formula (I) or (II) having an increased number of carbon atoms in the aliphatic chain is attributed to the decreased water solubility of such phosphorus compounds. The decreased water solubility assists the phosphorus compound to impart greater stability to the indicator reagent composition because they are more soluble in the second ethanolic dip that prevents crosscontamination effects during the manufacturing process of the test strip. The phosphorus compound is present to protect the indicator dye from the metal ion complex. Additionally, the aliphatic phosphorus compound may serve as an anionic wetting agent that stabilizes the oxidized, colored form of the indicator dye.

A phosphorus compound of general structural formula (I) or (II) wherein $R_1$ or $R_2$ is an aromatic moiety also imparts improved stability to the indicator reagent composition. The aromatic moiety can be a carbocyclic or a heterocyclic aromatic moiety, and includes aromatic moieties having fused rings. For example, the aromatic moiety can be derived from, but is not limited to derivation from, benzene, naphthalene, pyrrole, furan, pyrimidine, thiophene, pyridine, pyrazine, indole, quinoline, carbazole, purine, isoquinoline, isothiazole, isoxazole, and other similar carbocyclic and heterocyclic aromatic compounds. More specifically, a phosphorus compound useful in the present invention is depicted by structural formulas (III) and (IV), wherein Y is CH or N; and by structural formulas (V) and

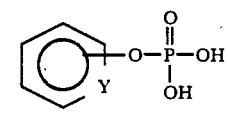
(III)

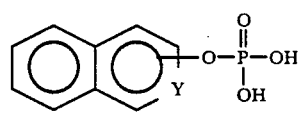
(IV)

VI, wherein Z is NH, O or S.

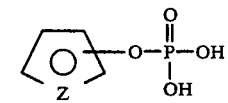
(V)

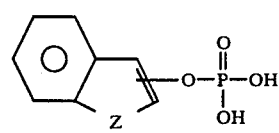
(VI)

The aliphatic moiety or the aromatic moiety of the phosphorus compound of general structural formula (I) or (II), $R_1$ or $R_2$ respectively, also can include a substituent group, or substituent groups, without adversely affecting the ability of the phosphorus compound to stabilize the indicator reagent composition of the present invention. The substituent group, or groups, can be positioned on any carbon of the aliphatic moiety, or at any position of the aromatic moiety, without adversely affecting the indicator reagent composition in an assay for a peroxidatively active substance. Substituent groups that can be included on the aliphatic moiety or on the aromatic moiety of the phosphorus compounds of general structural formulas (I) and (II) include, but are not limited to, nitro (—$NO_2$); cyano (—CN); halo (—Cl,—Br); amino (—$NH_2$); substituted amino (—$NHR_3$,—$NR_4R_5$ wherein $R_3$, $R_4$ and $R_5$ are substituted or unsubstituted aromatic or alkyl moieties including from one to about ten carbon atoms); hydroxy (—OH); alkoxy (—$OR_6$ wherein $R_6$ is a substituted or an unsubstituted alkyl group including from one to about ten carbon atoms); aryloxy (—$OR_7$ wherein $R_7$ is a substituted or an unsubstituted carbocyclic or heterocyclic aromatic ring system); sulfonate (—$SO_3H$); carbonyl (—CO—$R_8$ wherein $R_8$ is hydrogen, hydroxyl, an alkyl group, an aryl group, an alkoxy group, an aryloxy group, or an amino group); or a combination thereof.

In accordance with an important feature of the present invention, the phosphorus compound of general structural formula (I) or (II) includes a substituent $R_1$ or $R_2$ that is a residue of an aliphatic or of an aromatic polyhydric compound. A polyhydric compound has at least two hydroxy functionalities and includes classes of compounds such as glycols, triols, polyols, saccharrides and hydroxyphenols. Examples of residues of polyhydroxy compounds that are useful as a substituent on a phosphorus compound of general structural formula (I) or (II) include, but are not limited to, a residue of ethylene glycol, propylene glycol, butylene glycol, hexanediol, glycerol, neopentyl glycol, diethylene glycol, dipropylene glycol, triethylene glycol, cyclopentanediol, cyclohexanediol, hydrobenzoin, fructose, sorbitol, catechol, resorcinol and hydroquinone. Specific examples of phosphorus compounds of general structural formula (I) or (II) that include a residue of a polyhydric compound include the compounds illustrated in structural formulas (VII) through (X).

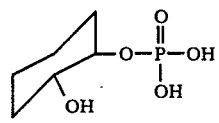
(VII)

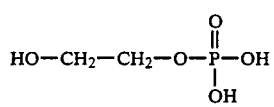
(VIII)

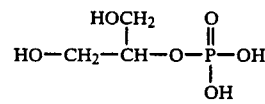
(IX)

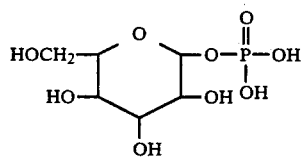
(X)

In particular, the compound of structural formula (VII) includes the residue of cyclohexanediol, whereas the compound of structural formula (VIII) includes the residue of ethylene glycol and the compound of structural formula (X) includes the residue of a monosaccharide, like glucose. To achieve the full advantage of the present invention, the phosphorus compound illustrated as structural formula (IX), including a residue of glycerol, and termed glyceryl-2-phosphate, is used as the phosphorus compound in the indicator reagent composition of the present invention.

Glyceryl-2-phosphate (IX) is a known compound. Surprisingly and unexpectedly, glyceryl-2-phosphate is included in a composition of the present invention to impart improved stability to the composition. Furthermore, when included in a composition of the present invention, either alone or with other known buffer agents, the buffering capabilities of glyceryl-2-phosphate also are demonstrated. As will be demonstrated more fully hereinafter, other buffer agents known to those skilled in the art can be included in the indicator reagent composition for their buffering capabilities, but these buffers did not stabilize the indicator reagent composition.

Therefore, the indicator reagent composition of the present invention, including an indicator dye, a hydroperoxide, a metal ion complex and a phosphorus compound of general structural formula (I) or (II), is utilized in an improved method to determine the presence or the concentration of a peroxidatively active substance in liquid test samples. It has been demonstrated that the indicator reagent composition interacts with a peroxidatively active substance to produce a differentiable and measurable color transition, either visually or by instrument. Furthermore, in addition to the essential ingredients described above, the indicator reagent composition of the present invention can include a sufficient amount of optional ingredients, like a buffer, such that the indicator dye changes color upon contact and interaction with the oxygen that is catalytically released from the hydroperoxide by the peroxidatively active substance. Accordingly, the color change accurately establishes the presence or concentration of a peroxidatively active substance in the test sample.

For example, test samples often have a pH outside the desired pH range for the assay of interest and therefore a buffer is added to the test composition. Accordingly, it has been demonstrated that any of various known types of buffers, if needed, can be included in the indicator reagent composition of the present invention. The buffer is especially important in a commercially-acceptable dry phase test strip that resists the effects of urine pH and urine specific gravity. The function of the buffer is to maintain the indicator reagent composition at a sufficient pH to maintain the stability of the indicator reagent composition and to produce the desired color transition in the indicator dye during the assay.

A buffer is included in the indicator reagent composition of the present invention usually in a concentration of between about 100 mM and about 500 mM, although in particular situations the concentration of the buffer can be above or below this range. It has been found that for optimum assay results, the pH of the indicator reagent composition generally should be maintained at a slightly acidic to a neutral pH value. Therefore, a pH of from about 5 to about 7, and preferably of from about 6 to about 7, provides a more spectacular and a more easily differentiable color transition in the assay for a peroxidatively active substances. However, present day assay methods for a peroxidatively active substance are performed at a slightly alkaline pH because the combination of an indicator dye, a hydroperoxide and ferric ion complex interacts prematurely at an acidic pH to give false positive assays. Surprisingly and unexpectedly, utilizing an indicator reagent composition of the present invention including a phosphorus compound of general structural formula (I) or (II) demonstrates sufficient stability such that the composition can be buffered at an acidic to a neutral pH.

For example, the prior art teaches that when a ferric ion complex, like Fe-HEDTA, is used to provide the desired ascorbate resistance, the indicator reagent composition is buffered above a pH of 6.5, like at a pH range of 6.7 from 7.1. Most preferably, the pH is buffered at 6.80 to 6.82. This pH range provided the best balance of sensitivity, stability and ascorbate resistance when assaying urine samples exhibiting highly variable pH values and specific gravity.

In accordance with an important feature of the present invention, it has been found that a phosphorus compound of general structural formula (I) or (II) can be used as the buffering agent, in addition to its utility in stabilizing the indicator reagent composition. The phosphorus compound can be used alone, or in combination with other well-known buffers such as acetate; phthalate; borate; trichloracetate; sulfosalicylate; phosphate; tartarate; citrate; succinate; 4-morpholinoethansulfonic acid; maleic acid; 2,2-bis(hydroxymethyl)-2,2',2"-nitrilotriethanol; 1,4-piperazinebis(ethanesulfonic acid); 3,3-dimethylglutaric acid; 3-N-morpholinopropanesulfonic acid (MOPS); malonic acid; 1,3-bis[tris(hydroxymethyl)methylamino]propane (Bis-tris); tris(hydroxymethyl)aminomethane (Tris); tris(hydroxymethyl)aminomethane-maleic acid (Tris-maleate); tris(hydroxymethyl)aminomethane-malonic acid (Tris-malonate); 3-N-(trishydroxymethyl)methylamino-2-hydroxypropanesulfonic acid (TAPSO); 2-([tris(hydroxymethyl)-methyl]amino)ethanesulfonic acid (TES); 1,4-piperazinebis(ethanesulfonic acid) (PIPES); 4-morpholinoethanesulfonic acid (MES); N-2-hydroxyethyl-piperazine-N'-2-ethanesulfonic acid (HEPES); and other suitable buffers as are well known in the art, or combinations thereof.

In addition to the indicator dye, the hydroperoxide, the metal ion complex and the phosphorus compound of general structural formula (I) or (II), other optional ingredients, in addition to the buffer, that do not materially alter the nature and the function of the four essential ingredients, and that do not interfere with the assay for a peroxidatively active substance, also can be included in the indicator reagent composition. For example, the indicator reagent composition optionally can include a compound to improve the wetting of the test pad of the test device by the test sample and to stabilize the oxidized indicator dye. This compound usually is an anionic surfactant or a nonionic surfactant. An anionic surfactant, such as a long carbon chain sulfate or sulfonate, like sodium dodecyl sulfate, dioctyl sodium sulfosuccinate and sodium dodecylbenzene sulphonate, is the preferred surfactant. Nonionic surfactants, such as an octoxynol, a nonoxynol or an ethoxylated fatty alcohol, also can be included in the indicator reagent composition of the present invention. The surfactant is included in the indicator reagent composition in a concentration of from 0 mM to about 200 mM, and preferably in a concentration of from about 50 mM to about 200 mM.

In addition to a surfactant, additional stabilizers can be included in the indicator reagent composition of the present invention. For example, a borate ester described by Lam in U.S. Pat. No. 4,071,318, hereby incorporated by reference, provides increased stability to the indicator dye present in the indicator reagent composition. Suitable borate esters include, but are not limited to, trimethanolamine borate, triethanolamine borate, tri(n-propanol)amine borate and tri(n-butanol)amine borate, or combinations thereof. To achieve the full advantage of the present invention, triisopropanolamine borate is included in the indicator reagent composition to further stabilize the indicator dye. The stabilizer is included in the indicator reagent composition in a concentration ranging from 0 mM to about 300 mM, and preferably in a concentration ranging from about 25 mM to about 200 mM.

The indicator reagent composition also can include a polymeric material that improves the stability and uniformity of the color transition of the test device. Furthermore, in a dry phase test strip, when the ingredients of the indicator reagent composition are incorporated into the test pad from two separate solutions, the polymeric material helps separate the ingredients present in the first impregnation solution from interacting with the ingredients present in the second impregnation solution. Accordingly, the test strip demonstrates increased stability. Suitable polymeric materials include, but are not limited to, polyvinyl pyrrolidone, polyvinyl alcohol, gum arabic, gelatin, algin, carrageenan, casein, albumin, methyl cellulose and similar natural and synthetic polymeric materials. The preferred polymeric material is a polyvinylpyrrolidone, such as PVP K-30, a polyvinylpyrrolidone of molecular weight 40,000 and available commercially from GAF Corp., New York, N.Y. The polymeric material generally is included in the indicator reagent composition in amounts ranging from 0% to about 5%, and preferably from about 1% to about 4% by total weight of the indicator reagent composition.

In addition, to improve the color resolution and differentiation of the color transition in a chromogenic assay for a peroxidatively active substance, inert background dyes can be included in the indicator reagent composition. Suitable background dyes include, but are not limited to, ethyl orange (4-(4-diethylaminophenylazo)benzenesulfonic acid); Orange G (4-(2-hydroxy-(7,9 sodium disulfonate)-1-naphthylazo)benzene); disperse orange 11, 13, or 25; calcomine orange; methyl orange; and orange II (4-(2-hydroxyl-1-naphthylazo)benzenesulfonic acid), or combinations thereof. A background dye is included in the indicator reagent composition of the present invention in a concentration ranging from 0 mM to about 2 mM, and preferably ranging from about 0.1 mM to about 1.2 mM.

The indicator reagent composition also can include a promoter to achieve a more sensitive assay for a peroxidatively active substance in a test sample. Promoters are known in the art of assaying for a peroxidatively active substance and include quinolines and isoquinolines, and their derivatives. U.S. Pat. No. 3,853,472 fully describes the quinolines and isoquinolines that are useful as promoters, and is hereby incorporated by reference. Accordingly, isoquinoline, 4-bromoisoquinoline, 4-methylquinoline, 6-methoxyquinoline, 3-aminoquinoline or 5,6-benzoquinoline are the preferred promoters. To achieve the full advantage of the present invention, 4-methylquinoline, available under the brand name LEPIDINE ® from Aldrich Chemical Co., Milwaukee Wis., or 6-methoxyquinoline is used as the reaction promoter. A promoter generally is included in the indicator reagent composition in a concentration ranging from 0 mM to about 125 mM, and preferably in a concentration ranging from about 25 mM to about 110 mM. It also should be understood that other optional ingredients, as are well known to those skilled in the art of diagnostic assays, also can be included in the indicator reagent composition.

The carrier vehicle for the ingredients included in the indicator reagent composition includes water. However, because of the limited water solubility of particular ingredients included in the indicator reagent composition, organic solvents such as methanol, ethanol, isopropyl alcohol, acetone, dimethylformamide, dimethylsulfoxide, acetonitrile, ethyl acetate and similar solvents can be included in the carrier vehicle. The selection of a suitable organic solvent or solvents, in addition to water, to include in the carrier vehicle of the indicator reagent composition is within the capability of those skilled in the art of designing diagnostic assays.

The amount of organic solvent present in the indicator reagent composition generally is in the range of from 0% to about 90%, and preferably from about 10% to about 70%, by weight of the carrier vehicle. A carrier solvent comprising water and an organic solvent, like ethanol or acetonitrile, is especially preferred because a carrier matrix impregnated with the indicator reagent composition can be dried within a few to several minutes.

As previously described, the indicator reagent composition undergoes a color transition upon contact with a test sample to demonstrate the presence of a peroxidatively active substance. Furthermore, the intensity and degree of the color transition are used to determine the quantitative concentration of a peroxidatively active substance in the test sample by comparing or correlating the color produced by the test sample to colors produced by solutions having a known concentration of the peroxidatively active substance. In accordance with an important feature of the present invention, it has been demonstrated that an indicator reagent composition of the present invention provides a sufficiently resolved and differentiated color transition such that the amount of a peroxidatively active substance in a test sample can be measured and accurately determined without the use of color-measuring instruments, such as spectrophotometers or colorimeters. However, if desired, such color-measuring instruments can be used to measure the difference in color degree and intensity between the test sample and a solution having a known concentration of a peroxidatively active substance.

Accordingly, an assay for a peroxidatively active substance that utilizes an indicator reagent composition of the present invention improves the accuracy and reliability of the assay and also increases physician confidence in the assay. Additionally, because of the number of urine assays for a peroxidatively active substance being performed at home by the untrained patient, as opposed to trained physicians or technicians in the laboratory, it is imperative to provide accurate and reliable quantitative assay methods for the peroxidatively active substance content in the urine.

To demonstrate the new and unexpected results achieved by the method of the present invention, various indicator reagent compositions of the present invention first were prepared, then used in an aqueous, wet phase assay for the content of a peroxidatively active substance in a test sample. In each of the compositions of Examples 1 through 10, the identity and the amount of the indicator dye, the hydroperoxide and the ferric ion complex remained constant. In addition, the amount of the phosphorus compound of general structural formula (I) or (II) included in the composition, except for the control experiment (Example 1), was constant, however, the identity of the particular phosphorus compound present in each example was changed. Accordingly, the indicator reagent compositions used in Examples 1 through 10 each were prepared to include the following concentration of ingredients, except that the indicator reagent composition used in Example 1 included a 0 mM concentration of the phosphorus compound. The indicator reagent compositions used in Examples 9 and 10 included a phosphorous compound that does not have a general structural formula (I) or (II).

INDICATOR REAGENT COMPOSITION
Formulation #1

| Ingredient | Concentration (mM) |
|---|---|
| Phosphorus Compound | 100 (except Ex. 1 = 0 mM) |
| 3,3',5,5'-Tetramethyl-benzidine (TMB) | 62.5 |
| Diisopropylbenzene-dihydroperoxide (DBDH) | 125 |
| Ferric chloride hexahydrate | 9.3 |
| N-(2-hydroxyethyl)ethylene-diaminetriacetic acid | 9.3 |
| N-(2-acetamido)imino-diacetic acid (ADA) | 100 |

The indicator reagent compositions used in Examples 1 through 10 were prepared by thoroughly admixing one part of an aqueous solution of a phosphorus compound, buffered at pH 5.8, with two parts of a 90:10 by weight acetonitrile:water solution that included the remaining composition ingredients. Consequently, the indicator reagent compositions used in Examples 1 through 10 included a 60:40 by weight acetonitrile:water carrier vehicle and further included the concentration of ingredients listed in Formulation #1 in millimoles per liter of solution (mM). TABLE I lists the particular phosphorus compound of general structural formula (I) or (II) included in the indicator reagent compositions utilized in Examples 1 through 10.

TABLE I
Phosphorus Compound Utilized in Wet Phase Assay for a Peroxidatively Active Substance

| Example | Phosphorus Compound |
|---|---|
| 1 | None |
| 2 | Phosphonic Acid ($R_2$ = H) |
| 3 | Phenyl Dihydrogen Phosphate ($R_1$ = $C_6H_5$) |
| 4 | p-Nitrophenyl Dihydrogen Phosphate ($R_1$ = p-$NO_2$—$C_6H_5$) |
| 5 | 2-Glyceryl Dihydrogen Phosphate ($R_1$ = $C_3H_7O_2$) |
| 6 | Ethyl Dihydrogen Phosphate ($R_1$ = $C_2H_5$) |
| 7 | Phosphoric Acid ($R_1$ = H) |
| 8 | Phenylphosphonic Acid ($R_2$ = $C_6H_5$) |
| 9 | Diphenyl Hydrogen Phosphate (($C_6H_5O)_2$—P(O)(OH) |
| 10 | Triphenyl Phosphate ($C_6H_5O)_3$—P(O) |

TABLE II illustrates and summarizes the results of a wet phase assay of aqueous test samples that do not include a peroxidatively active substance. Accordingly, because a peroxidatively active substance is absent, an indicator reagent composition used in a wet phase assay to detect a peroxidatively active substance should not undergo a color transition. Therefore, in each of Examples 1 through 10, a previously-described indicator reagent composition was added to a test sample that lacked a peroxidatively active substance, and the change in color of the assay was monitored over time. In particular, in Examples 1 through 10, an indicator reagent composition first was added to a UV-VIS (ultra-violet visual) cuvette, then a test sample absent a peroxidatively active substance was added to the cuvette. The color transition of the assay solution in the UV-VIS cuvette then was monitored over time at 660 nanometers (nm), and the rate of color transition (i.e., change in absorbence per minute) was calculated by standard procedures known to those in the art.

TABLE II
Rate of Color Transition For Test Samples Absent A Peroxidatively Active Substance

| Example | Change in Absorbence per Minute (660 nm) |
|---|---|
| 1 | 4.50 |
| 2 | 0.19 |
| 3 | 0.06 |
| 4 | 0.08 |
| 5 | 0.40 |
| 6 | 1.40 |
| 7 | 1.72 |
| 8 | 1.98 |
| 9 | 5.61 |
| 10 | 5.48 |

From TABLE II, it is observed that in Example 1, an assay that used an indicator reagent composition absent a phosphorus compound depicted by general structural formulas (I) and (II), underwent a large color transition even though a peroxidatively active substance was not present. In visual terms, the assay solution turned blue, thereby indicating the presence of a peroxidatively active substance. The indicator reagent composition used in Example 1, excluding a phosphorus compound of general structural formula (I) or (II), underwent a sufficiently large color transition such that the detection limit of the measuring instrument was approached. Accordingly, if a test sample including a peroxidatively active substance was assayed with the composition utilized in Example 1, the peroxidatively active substance could not be detected in a wet phase assay because of the large background absorbence. This result is in accordance with observations disclosed in the prior art wherein wet phase assays were considered impractical to impossible because the reaction between the indicator dye (TMB) and the hydroperoxide (DBDH) was catalyzed by the ferric ion complex (Fe-HEDTA) in aqueous solution.

However, surprisingly and unexpectedly, when an indicator reagent composition of the present invention, comprising an indicator dye, a hydroperoxide, a metal ion complex and a phosphorus compound of general structural formula (I) or (II), is used in a wet phase assay for a peroxidatively active substance, the indicator reagent composition imparts sufficient stability to the indicator reagent composition to allow the detection and measurement of a peroxidatively active substance in a test sample in aqueous solution. Accordingly, in Examples 2 through 8, an indicator reagent composition of the present invention was used in a wet phase assay for a peroxidatively active compound. The indicator reagent compositions utilized in the assays of Examples 2 through 8 demonstrated a substantially smaller, to negligible, background color formation thereby permitting the detection of a peroxidatively active substance in a test sample by a wet phase assay procedure. For example in Example 8, the change in absorbence per minute is only 1.98, compared to 4.50 for the composition used in the assay of Example 1. Even more surprisingly, Example 2 and Example 3 demonstrated an essentially negligible change in absorbence per minute of 0.06 and 0.08. Because the stability of the indicator reagent compositions of the present invention, it was found that the indicator reagent compositions developed a sufficiently low background color in a wet phase assay such that test samples having a hemoglobin concentration as low as 0.010 mg/dL generated a detectable and measurable color transition. Accordingly, a wet phase assay method, either qualitative or quantitative, for a peroxidatively active substance in a test sample is achieved. In addition, for the indicator reagent compositions used in Examples 2 through 8, it was found that in assays performed on test samples including a peroxidatively active substance, the change in absorbence increased in direct proportion to the amount of hemoglobin in the test sample. Furthermore, the indicator reagent compositions of the present invention utilized in Examples 2 through 8 demonstrated a sufficient ascorbate resistance such that in a test sample including 109 mM ascorbic acid essentially did not effect on the absorbence measurement of a test sample including 0.045 mg/dL hemoglobin.

TABLE II also shows that the indicator reagent compositions utilized in Examples 2 through 5 demonstrated an exceptional ability to resist premature oxidation of the background dye, and therefore to essentially eliminate the development of a background color. However, the indicator reagent compositions of the present invention utilized in Examples 6 through 8 also demonstrated an improved ability to resist premature oxidation of the indicator dye, and therefore to help eliminate false positive assays. Although the results demonstrated in Examples 6 through 8 are not as dramatic as the results demonstrated by Examples 2 through 5, the indicator reagent compositions utilized in Examples 6 through 8 nevertheless are useful in the wet phase assay method of the present invention, especially in a qualitative assay for a peroxidatively active substance in a test sample.

Furthermore, the assay results provided by the indicator reagent compositions used in Examples 2 through 8 should be compared to the results of the assays of Examples 9 and 10. In Examples 9 and 10, the wet phase assays used an indicator reagent composition that included a phosphorus compound having less than two free acid functionalities. From TABLE II, it is seen that such phosphorus compounds demonstrate a destabilizing effect on the indicator reagent composition, whereby the indicator reagent composition developed a more intense background color, more quickly, than an indicator reagent composition absent a phosphorus compound (EX. 1). Accordingly, the method and composition of the present invention requires that the indicator reagent composition includes a phosphorus compound of general structural formula (I) or (II) having at least two free acid functionalities. Furthermore, TABLE II demonstrates that an accurate and reliable wet phase assay for a peroxidatively active substance is provided when the phosphorus compound included in the indicator reagent compound has a substituent $R_1$ or a substituent $R_2$ of compound (I) or compound (II) that is hydrogen (Examples 2 and 7), a substituted or an unsubstituted alkyl or aryl moiety (Examples 3, 4, 6 and 8) or a residue of a polyhydric compound (Example 5).

Therefore, the indicator reagent composition of the present invention provides a wet phase assay for a peroxidatively active substance. However, in addition to the wet phase assay for a peroxidatively active substance, the indicator reagent composition also can be used in dry phase test strip assay for a peroxidatively active substance. The dry phase test stip assay for a peroxidatively active substance that utilizes the indicator reagent composition of the present invention is performed in accordance with methods well known in the art. In general, the assay for a peroxidatively active substance is performed by contacting the urine or other test sample with an analyte detection device that includes the indicator reagent composition. The analyte detection device can be dipped into the test sample, or the test sample can be applied to the analyte detection device dropwise. The resulting change in color of the analyte detection device demonstrates the presence of a peroxidatively active substance; and, if so designed, the resulting color transition can be compared to a standardized color chart to provide a quantitative measurement of the concentration of a peroxidatively active substance in the urine or test sample.

Typically, the analyte detection device is a reagent impregnated test strip, designed either as a single pad test strip (to assay only for a single analyte) or as a multiple pad test strip (to assay for several analytes simultaneously). For either type of reagent impregnated test strip, the test strip includes a support strip, or handle, normally constructed from a hydrophobic plastic, and a reagent test pad, comprising a bibulous or a nonbibulous carrier matrix incorporating the indicator reagent composition. In general, the carrier matrix is an absorbent material that allows the test sample to move, in response to capillary forces, through the carrier matrix to contact the indicator reagent composition and produce a detectable or measurable color transition.

The carrier matrix can be any substance capable of incorporating the chemical reagents required to perform the assay of interest, as long as the carrier matrix is substantially inert with respect to the chemical reagents, and is porous and/or absorbent relative to the liquid test sample. The expression "carrier matrix" refers to either bibulous or nonbibulous matrices that are insoluble in water and other physiological fluids and maintain their structural integrity when exposed to water and other physiological fluids. Suitable bibulous matrices include filter paper, sponge materials, cellulose, wood, woven and nonwoven fabrics and the like. Nonbibulous matrices include glass fiber, polymeric films, and preformed or microporous membranes. Other suitable carrier matrices include hydrophilic inorganic powders, such as silica gel, alumina, diatomaceous earth and the like; argillaceous substances; cloth; hydrophilic natural polymeric materials, particularly cellulosic material, like cellulosic beads, and especially fiber-containing papers such as filter paper or chromatographic paper; synthetic or modified naturally-occurring polymers, such as cellulose acetate, polyvinyl chloride, polyacrylamide, polyacrylates, polyurethanes, crosslinked dextran, agarose, and other such crosslinked and noncrosslinked water-insoluble hydrophilic polymers. Hydrophobic and nonabsorptive substances are not suitable for use as the carrier matrix of the present invention. The carrier matrix can be of different chemical compositions or a mixture of chemical compositions. The matrix also can vary in regards to smoothness and roughness combined with hardness and softness. However, in every instance, the carrier matrix must include a hydrophilic or absorptive material. The handle usually is formed from hydrophobic materials such as cellulose acetate, polyethylene, terephthalate, polycarbonate or polystyrene, and the carrier matrix is most advantageously constructed from bibulous filter paper or nonbibulous polymeric films.

If the test strip is designed to assay for a peroxidatively active substance in a test sample, the carrier matrix can be any bibulous or nonbibulous material that allows permeation by the test sample to saturate the test pad of the test strip that is impregnated with the indicator reagent composition. To achieve the full advantage of the present invention, in the assay for a peroxidatively active substance, the carrier matrix is a hydrophilic, bibulous matrix, including cellulosic materials, such as paper, and preferably filter paper. Filter paper possesses all of the qualities required of a bibulous matrix of the present invention, plus the advantages of abundant supply, favorable economics, and a variety of suitable grades. Filter paper has been found to be extremely satisfactory for use as a matrix material for suspending and positioning both the essential ingredients and any optional ingredients included in the indicator reagent composition.

To achieve the full advantage of the present invention, the indicator reagent composition is impregnated into a suitable carrier matrix and utilized in a dry phase test strip for the assay of a peroxidatively active substance in a test sample. The method of the present invention affords an economical, accurate and reliable assay for the presence or concentration of a peroxidatively active substance in a test sample that can be performed at home or in the laboratory. In addition, the method of the present invention allows detection, differentiation and measurement of a low concentration of a peroxidatively active substance in the test sample therefore making the assay more useful clinically.

In accordance with the method of the present invention, to perform a dry phase test strip assay for a peroxidatively active substance, an aqueous solution, including from about 50 mM to about 500 mM concentration of a phosphorus compound of general structural formula (I) or (II); from about 0.5 mM to about 50 mM of a metal ion complex; from about 100 mM to about 500 mM of a buffer; from 0 mM to about 300 mM of a stabilizer; from 0 mM to about 200 mM of a surfactant; and any other desired optional ingredients or solvents, first is prepared. This aqueous solution then is adjusted to a pH of from about 6 to about 7 with a suitable organic or mineral acid, such as 1N hydrochloric acid. A bibulous matrix, such as filter paper, then is saturated and impregnated with the aqueous solution by immersing or by spraying the aqueous solution onto sheets or precut strips of the filter paper.

Then, after removing the aqueous solvent by drying in an air oven at a temperature of from about 40° C. to about 100° C. for about 20 minutes, the filter paper is saturated and impregnated with a second ethanolic solution including from about 5 mM to about 60 mM of an indicator dye; from about 5 mM to about 100 mM of a hydroperoxide; from 0% to about 5% of a polymeric material; from 0 mM to about 125 mM of a promoter; and any other desired optional ingredients or solvents, like background dyes, either by immersion or by spraying. After a second oven drying at about 40° C. to about 100° C. for approximately 20 minutes, the twice-impregnated filter paper is cut to an appropriate size, such as a pad having dimensions from about 0.25 cm by about 0.5 cm to about 0.5 cm by about 1.0 cm. The dried, twice-impregnated filter paper then is secured to an opaque or transparent hydrophobic plastic handle with double sided adhesive tape. The resulting test strip then is dipped into a fresh, uncentrifuged urine sample for a sufficient time to saturate the test pad with the sample. After waiting a predetermined time, such as from about 15 secs. to about 60 secs., the test strip is examined, either visually or by instrument, for a response. The color transition, if any, of the test pad reveals the presence or concentration of a peroxidatively active substance in the urine sample.

Analogous to the wet phase assay for a peroxidatively active substance described above, it is well within the experimental techniques of those skilled in the art of preparing test devices to determine the proper balance between size of reagent pad, the strength of reagent impregnating solutions, the amount of test sample, and the method of introducing the test sample to the test strip, such as by pipetting rather than dipping, in order to design a quantitative assay for a peroxidatively active substance utilizing the method and composition the present invention.

In many cases, simple visual observation of the test strip provides the desired information. If more accurate information is required, a color chart bearing color spots corresponding to various known concentrations of a peroxidatively active substance can be prepared for the particular indicator reagent composition used in the test strip. The resulting color of the test strip after contact with the urine sample then can be compared with the color spots on the chart to determine the concentration of a peroxidatively active substance in the test sample.

If a still more accurate determination is required, a spectrophotometer or colorimeter can be used to more precisely determine the degree of color transition. In addition, both the wet phase assay and the dry phase test strip assay can be made quantitative by employing spectrophotometric or colorimetric techniques, as opposed to visual techniques, in order to more reliably and more accurately measure the degree of color transition, and therefore more accurately measure the concentration of a peroxidatively active substance in the test sample, especially at lower protein concentrations, such as below 0.010 mg/dL.

Therefore, in accordance with an important feature of the present invention, it has been demonstrated that by impregnating an indicator reagent composition of the present invention into a suitable carrier matrix, the presence or concentration of a peroxidatively active substance in a test sample can be achieved by using a dry phase test strip. As previously discussed, a dry phase test strip used for the assay of a peroxidatively active substance in a test sample generally includes a carrier matrix comprising any absorbent matrix that is amenable to treatment and impregnation with the indicator reagent composition; that permits the urine or other test sample to permeate the carrier matrix rapidly enough to obtain a reliable assay relatively quickly; and that does not contaminate the urine or other test sample either by test sample extraction of components comprising the carrier matrix or by appreciably altering the urine or test sample in a way to make the subsequent assay inconclusive, inaccurate or doubtful.

In accordance with one embodiment of the present invention, the following dry phase test strip was prepared to perform a dry phase assay for a peroxidatively active substance. A strip or a sheet of a carrier matrix, like filter paper, such as WHATMAN CCP500, available from Whatman Inc., Maidenhead, Kent, U.K., first was immersed into an aqueous solution including:

| INDICATOR REAGENT COMPOSITION Formulation #2 First Immersion Solution | |
|---|---|
| Ingredient | Concentration |
| Glyceryl-2-phosphate (Phosphorus compound) | 200 mM |
| Ferric chloride (Metal ion) | 5.1 mM |
| N-(2-hydroxyethyl)ethylene-diaminetetraacetic acid (Complexing agent for the metal ion) | 5.1 mM |
| Triisopropanolamine borate (Stabilizer) | 250 mM |
| Sodium Dodecyl Sulfate (Surfactant) | 28 mM |
| Hydrochloric Acid (1N) | to adjust pH to 6.4 |

The once impregnated-filter paper matrix then was dried in an oven having a temperature ranging from about 45° C. to about 60° C. After drying, the once-impregnated filter paper then was immersed into an ethanolic solution including:

| Second Immersion Solution | |
|---|---|
| Ingredient | Concentration |
| Tetramethylbenzidine (TMB) (Indicator Dye) | 34.7 mM |
| Diisopropylbenzenedihydroperoxide (DBDH) (Hydroperoxide) | 65.0 mM |
| 4-Methylquinoline (Promoter) | 61.3 mM |
| Ethyl Orange (Inert Background Dye) | 0.69 mM |
| Orange G (Inert Background Dye) | 0.55 mM |

The twice-impregnated filter paper matrix then was dried in an oven having a temperature ranging from about 40° C. to about 60° C. The dried and twice-impregnated filter paper then was cut into a pad having dimensions of about 0.5 cm by about 0.5 cm to provide a test pad comprising a carrier matrix impregnated with an indicator reagent composition of the present invention. In addition, it should be understood that the indicator reagent composition of the present invention demonstrates sufficient stability such that the carrier matrix can be impregnated by immersing the carrier matrix into an aqueous solution including all of the essential and optional ingredients of the indicator reagent composition. However, the two step method utilizing two immersions is preferred because contact between the indicator dye and the metal ion complex is minimized, and therefore a premature interaction is precluded.

To demonstrate the new and unexpected results achieved by the method of the present invention, dry phase test strips incorporating an indicator reagent composition of the present invention were used in a dry phase assay for a peroxidatively active substance. The dry phase test strips were produced as described above, then dipped into a test sample. Individual test samples either included or lacked a peroxidatively active substance, i.e., hemoglobin. After contacting the test sample, the reflectance of the test pad of the test strip then was measured at 660 nm on an Advanced Research Rapid Scanner reflectance spectrometer, of the Diagnostics Division of Miles, Inc., Elkhart, Ind. To serve as a blank control assay, a test strip was dipped into water, then the reflectance was measured at 660 nm approximately ten minutes after dipping the test strip into the water. This reflectance measurement represented the degree and intensity of a blank reaction. Similarly, the reflectance of a test strip dipped into a urine sample including 0.045 mg/dL of hemoglobin was measured at 660 nm approximately one minute after dipping the test strip into the urine sample. This reflectance measured represented the reactivity of the test strip in the presence of a peroxidatively active substance.

It was demonstrated that a test pad including an indicator reagent composition of the present invention has excellent stability, i.e., does not undergo a color transition after storage for at least 28 days at about 50° C.; does not provide false positive assays upon contacting a test sample absent a peroxidatively active substance, and retains its reactivity and sensitivity over extended time periods, i.e., after storage for 8 weeks at 50° C., a composition of the present invention still accurately detects 0.045 mg/dL hemoglobin in a test sample. For example, the reflectance of a test pad including the above-described composition of the present invention, including glyceryl-2-phosphate as the phosphorus compound, remained essentially constant ten minutes after dipping the test pad into a water sample. Accordingly, the indicator reagent composition of the present invention did not undergo a color transition upon contacting a test sample absent a peroxidatively active substance. An identical test strip was dipped into a test sample including a peroxidatively active substance and underwent a detectable and measurable color transition as demonstrated by a change in reflectance one minute after dipping the test pad into a test sample.

In contrast, a test strip comprising a test pad incorporating an indicator reagent composition that did not include a phosphorus compound of general structural formula (I) or (II), but included instead 200 mM of either 4-morpholinoethanesulfonic acid, maleic acid, 2,2-bis(hydroxymethyl)-2,2',2''-nitrilotriethanol, 1,4-piperazinebis(ethanesulfonic acid) or 3,3-dimethylglutaric acid, demonstrated an approximately 15% to approximately 20% change in reflectance ten minutes after dipping the test strip into a water sample. Visually, this large percentage change in reflectance corresponds to a sufficient color transition such that a false positive assay, or an erroneously high assay, for a peroxidatively active substance results. Furthermore, the pH of each of the above assays was maintained to within about 0.05 of the pH of the assay wherein glyceryl-2-phosphate was included in the indicator reagent composition. Consequently, a pH difference was eliminated as the cause for the color transition. Therefore, when an indicator reagent composition is lacking a phosphorus compound of general structural formula (I) or (II), the resulting test strip demonstrated an unacceptably large change in reflectance, or color transition, that leads to a false positive assay of a test sample that does not include a peroxidatively active substance.

The above-described test results are summarized in TABLE III, wherein various indicator reagent compositions were incorporated into dry phase test strips and used to assay a test sample for a peroxidatively active substance. Specifically, the data summarized in TABLE III show that if an indicator reagent composition of the present invention (C) is used, then the difference in percent reflectance one minute after contacting a test sample containing 0 mg/dL hemoglobin and a test sample containing 0.015 mg/dL hemoglobin is about 30 to about 35 units, i.e., 65.5% compared to 29.6%, or 68.5% compared to 34.8%. This large change in percent reflectance allows the assayer to determine whether the test sample includes no hemoglobin (a negative assay) or includes a trace amount of hemoglobin (0.015 mg/dL). However, when the indicator reagent composition D is used, the difference in percent reflectance is only about an inconsistent 5 to 15 units, thereby making the determination of whether the test sample includes 0 mg/dL hemoglobin or 0.015 mg/dL hemoglobin difficult to impossible. Accordingly, the accuracy and sensitivity of an assay for a peroxidatively active substance is substantially improved by including a phosphorus compound of general structural formula (I) or (II) in the indicator reagent composition.

TABLE III

HEMOGLOBIN ASSAY OF STANDARDIZED TEST SAMPLES

| Hemoglobin Concentration (mg/dL) | Ascorbate Concentration (mg/dL) | Stress Condition | Indicator Reagent Composition | | | |
|---|---|---|---|---|---|---|
| | | | A | B | C | D |
| | | | (% Reflectance at 600 nm and one minute after contacting the test sample) | | | |
| 0 | 0 | 1 | 50.5 | 65.2 | 65.5 | 42.1 |
| 0 | 0 | 2 | 53.1 | 63.4 | 68.5 | 32.1 |
| 0.015 | 0 | 1 | 26.0 | 29.3 | 29.6 | 36.7 |
| 0.015 | 0 | 2 | 49.2 | 48.2 | 34.8 | 47.3 |
| 0.045 | 0 | 1 | 14.4 | 18.3 | 20.1 | — |
| 0.045 | 0 | 2 | 28.1 | 31.6 | 21.1 | — |
| 0.045 | 0 | 3 | 15.3 | 59.3 | 21.8 | — |
| 0.045 | 50 | 1 | 61.2 | 26.3 | 24.6 | — |
| 0.045 | 50 | 2 | 61.9 | 52.8 | 33.6 | — |

Indicator Reagent Composition
A Present-day HEMASTIX ® reagent;
B Formulation #2, with triethanol amine borate and malonic acid
C Formulation #2;
D Formulation #2, but absent glyceryl-2-phosphate.
Stress Condition
1 Freshly prepared test strip;
2 Test strip stored for 28 days at 50° C.
3 Test strip exposed for 10 minutes at 30° C. and 45% relative humidity after contacting the test sample.

To further demonstrate that an indicator reagent compound of the present invention including a phosphorus compound of general structural formula (I) or (II) has increased stability and therefore essentially eliminates the problem of a false positive assay, the glyceryl-2-phosphate in the indicator reagent composition was replaced by other known buffers in order to examine the stabilizing effect provided by the phosphorus compound. Then, test strips including either glyceryl-2-phosphate or another known buffer contacted a test sample and the change in reflectance of the test strip was monitored over time. The results are summarized in TABLE IV wherein the indicator reagent composition of Formulation #2 was utilized, but the glyceryl-2-phosphate incorporated to stabilize the indicator reagent composition and to serve as a buffer, was replaced by another buffer. The test strips were dipped into a test sample that did not include a peroxidatively active substance (water), and the reflectance was measured at 660 nm approximately ten minutes after contact between the test strip and the test sample.

TABLE IV

BACKGROUND COLOR DEVELOPMENT OF DRY PHASE TEST STRIPS (pH = 6.7)

| Buffer | pKa of Buffer | Change in Reflectance (at 660 nm) |
|---|---|---|
| Malonic Acid | 5.8 | 1.60 |
| Maleic Acid | 6.3 | 2.82 |
| Bistris | 6.5 | 1.56 |
| Citric Acid | 6.4 | 1.91 |

TABLE IV-continued

BACKGROUND COLOR DEVELOPMENT OF DRY PHASE TEST STRIPS (pH = 6.7)

| Buffer | pKa of Buffer | Change in Reflectance (at 660 nm) |
|---|---|---|
| PIPES | 6.8 | 1.44 |
| MES | 6.2 | 2.46 |
| Dimethyl glutaric acid | 6.3 | 2.42 |
| Glyceryl-2-phosphate | 6.7 | −0.03 |

The data summarized in TABLE IV demonstrate that a test strip incorporating an indicator reagent composition of the present invention, incorporating a phosphorus compound of general structural formula (I) or (II), like glyceryl-1-phosphate, does not develop a background color over time (i.e., the change in reflectance is −0.03), whereas the other buffers generate a sufficient background color (i.e., a change in reflectance from 1.44 to 2.92) to interfere in the quantitative assay for a peroxidatively active substance. Consequently, a test pad that includes an indicator reagent composition lacking a phosphorus compound of general structural formula (I) or (II) can provide a false positive assay for a test sample absent a peroxidatively active substance, or an erroneously high assay for a test sample including a peroxidatively active substance.

Therefore, to achieve the full advantage of the present invention, the assay of a test sample for a peroxidatively active substance is performed with a dry phase test strip including a test pad comprising a suitable carrier matrix impregnated with an indicator reagent composition comprising:

| | |
|---|---|
| Glyceryl-2-phosphate | 225 mM |
| 3-N-Morpholinopropanesulfonic acid | 225 mM |
| Ferric chloride | 7.5 mM |
| N-(2-hydroxyethyl)ethylenediaminetriacetic acid | 7.5 mM |
| Triisopropanolamine borate | 125 mM |
| Sodium Dodecyl Sulfate (SDS) | 100 mM |
| Polyvinylpyrrolidone | 2.5% by weight |
| 3,3',5,5'-Tetramethylbenzidine (TMB) | 34.7 mM |
| 1,4-Diisopropylbenzene di- | 65.0 mM |

| | |
|---|---|
| hydroperoxide (DBDH) | |
| 4-Methylquinoline (LEPIDINE ®) | 105 mM |
| 4-(4-Diethylaminophenylazo)-benzenesulfonic acid (Ethyl Orange) | 0.69 mM |
| 4-(2-Hydroxy-(7,9-sodium-disulfonate)-1-naphthylazo)-benzene (Orange G) | 0.55 mM |
| Water | q.s. |
| Adjust pH to 6.3 with 1N HCl | |

The assay results for a peroxidatively active substance are both surprising and unexpected when an indicator reagent composition of the present invention, including a phosphorus compound of general structural formula (I) or (II) either as the buffer or in combination with other buffers, is used in a dry phase test strip assay. The development of a blank color in dry phase test strips for a peroxidatively active substance, a continuing and substantial problem in prior art assay methods, such as assay methods for occult blood that also provide ascorbate resistance, is essentially eliminated. The discovery of an indicator reagent composition that essentially eliminates the development of a blank color, and therefore essentially eliminates the problem of a false positive assay, is an unexpected improvement in the art of wet phase and dry phase test strip assays for a peroxidatively active substance. The indicator reagent composition essentially eliminates false positive assays and therefore improves assay sensitivity, especially to low concentrations of a peroxidatively active substance. Therefore, in accordance with an important feature of the present invention, more accurate and reliable assays for a peroxidatively active substance in urine and other test samples can be performed by utilizing the indicator reagent composition of the present invention.

The method and composition of the present invention prevent the metal ion complex and the hydroperoxide from prematurely oxidizing the indicator dye, thereby providing a more stable indicator reagent composition that undergoes a color transition in response to the concentration of a peroxidatively active substance in a test sample. In general, an indicator reagent composition of the present invention including a phosphorus compound of general structural formula (I) or (II) prevents the development of a premature background color due to an interaction between a metal ion complex, a hydroperoxide and an indicator dye; prevents premature indicator dye oxidation in both wet phase and dry phase test strip assays employing an indicator dye, a metal ion complex, and a hydroperoxide; permits buffering the wet phase and the dry phase assay at an acidic pH to provide a more spectacular color development; provides a wet phase assay for a peroxidatively active substance utilizing an indicator dye, a metal ion complex and a hydroperoxide; does not interfere with indicator dye oxidation by a peroxidatively active substance and a hydroperoxide; and does not interfere with ascorbate resistance provided by the metal ion chelate and a hydroperoxide.

Obviously, many modifications and variations of the invention as hereinbefore set forth can be made without departing from the spirit and scope thereof and therefore only such limitations should be imposed as are indicated by the appended claims.

I claim:

1. A solid state test device composition capable of exhibiting a sufficient color transition upon contacting a test sample to demonstrate the presence or concentration of a peroxidatively active substance in the test sample consisting essentially of:
   (a) a redox indicator selected for the group consisting of benzidine; 3,3',5,5'-tetraalkylbenzidine, wherein the alkyl group includes from one to six carbon atoms; 2,7-diaminofluorene; bis-(N-ethyl-quinol-2-one)-azine; (N-methylbenzthiazol-2-one)-(1-ethyl-3-phenyl-5-methyltriazol-2-one)-azine; and combinations thereof;
   (b) an organic hydroperoxide selected for the group consisting of cumene hydroperoxide, t-butyl hydroperoxide, diisopropylbenzene dihydroperoxide, 1-hydroxycyclohexane-1-hydroperoxide, 2,5-dimethylhexane-2,5-dihydroperoxide, paramethane hydroperoxide, 1,4-diisopropylbenzene monohydroperoxide, p-t-butylisopropylbenzene hydroperoxide, 2-(hydroperoxyisopropyl)-6-isopropylnaphthalene, tetralin hydroperoxide and combinations thereof;
   (c) a ferric ion complex;
   (d) a phosphorous compound having the formula

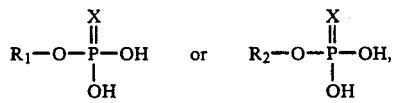

wherein $R_1$ or $R_2$ is a substituted or an unsubstituted aromatic moiety selected for the group consisting of benzene, naphthalene, pyrrole, furan, pyrimidine, thiophene, pyridine, pyrazine, indole, quinoline, carbazole, purine, and isoquinoline, or a polyhydric substituent selected from the group consisting of ethylene glycol, propylene glycol, butylene glycol, hexanediol, glycerol, neopentyl glycol, diethylene glycol, dipropylene glycol, triethylene glycol, cyclopentanediol, and cyclohexanediol; and wherein X is O, S or NH; and
   (e) a suitable carrier vehicle.

2. The composition of claim 1 wherein the ferric ion complex is selected from the group consisting of ferric ion complexes of N-(2-hydroxyethyl)ethylenediaminetriacetic acid, ethylenediaminetetraacetic acid, cyclohexylenediaminetetraacetic acid, nitrolotriacetic acid, iminodiacetic acid, ethylenediaminediacetic dipropionic acid, hydroxyethyliminodiacetic acid, diethylenetriaminepentaacetic acid, ethylene-bis(oxyethylenenitrilo)tetracetic acid, N-(2-acetamido)iminodiacetic acid, citric acid, gluconic acid, a glucoheptonate, bissalicylaldehydeethylenediamato, and combinations thereof.

3. The composition of claim 1 wherein the ferric ion complex is of N-(2-hydroxyethyl)ethylenediaminetriacetic acid.

* * * * *